United States Patent [19]

Gajewski et al.

[11] Patent Number: 4,505,708
[45] Date of Patent: Mar. 19, 1985

[54] BLOOD COMPONENT STORAGE CONTAINER AND METHOD UTILIZING A POLYVINYL CHLORIDE PLASTIC FORMULATION FREE OR ESSENTIALLY FREE OF LEACHABLE MATERIALS

[75] Inventors: Henry M. Gajewski, Winnetka; Paul Measells, Libertyville, both of Ill.

[73] Assignee: Baxter Travenol Laboratories, Inc., Deerfield, Ill.

[21] Appl. No.: 424,679

[22] Filed: Sep. 27, 1982

[51] Int. Cl.$^3$ .............................. A61J 1/00; A61M 5/00
[52] U.S. Cl. ..................................... 604/408; 604/403; 128/DIG. 24; 523/112
[58] Field of Search ............... 604/408, 403, 409, 410; 128/DIG. 24; 523/103, 105, 112; 524/569

[56] References Cited

U.S. PATENT DOCUMENTS

| | | |
|---|---|---|
| 2,275,957 | 3/1942 | Groff . |
| 2,868,745 | 1/1959 | Canarios . |
| 2,921,917 | 1/1960 | Longman . |
| 4,055,518 | 10/1977 | Kakitani et al. . |
| 4,072,790 | 2/1978 | Creekmore et al. . |
| 4,081,413 | 3/1978 | Tybus et al. . |
| 4,220,570 | 9/1980 | Loffelholz et al. . |
| 4,222,379 | 9/1980 | Smith . |
| 4,252,705 | 2/1981 | Brecker . |
| 4,269,743 | 5/1981 | Hulyalkar et al. . |
| 4,269,744 | 5/1981 | Hulyalkar et al. . |
| 4,280,497 | 7/1981 | Warner et al. . |
| 4,283,310 | 8/1981 | James et al. . |
| 4,286,597 | 9/1981 | Gajewski et al. .................. 604/403 |
| 4,300,559 | 11/1981 | Gajewski et al. .................. 604/403 |
| 4,301,800 | 11/1981 | Collins ............................. 604/403 |
| 4,329,992 | 5/1982 | Becker et al. ..................... 604/403 |
| 4,346,710 | 8/1982 | Thanawalla et al. ............... 604/403 |

FOREIGN PATENT DOCUMENTS

| | | | |
|---|---|---|---|
| 489541 | 1/1978 | Australia ........................... 604/408 |
| 584434 | 1/1947 | United Kingdom . |
| 1460221 | 12/1975 | United Kingdom . |

OTHER PUBLICATIONS

Chemical Abstracts 55CA20497c.
Chemical Abstracts 83CA158632f.
Chemical Abstracts 87136876u.
*Vinyl and Allied Polymers* (vol. 2), pp. 76, 77, 82 and 83.
"Mechanism of the Thermal Stabilization of Poly(vinyl chloride) with Middle Carboxylates and Epoxy Plasticizers", *Journal of Polymer Science*, vol. 8, pp. 2905-2922, (1970), Anderson et al.
"Synergistic Stabilization of PVC, *SPE Journal*, vol. 29, (Feb. 1973), Deanin et al.
Bergman, "Heat Stabilizers", *Modern Plastics Encyclopedia*, vol. 56, 10A, pp. 190 and 195, (Oct. 1979).
Irida et al., "Stabilization of Poly-Vinyl Chloride", Synergism between Metal Soaps and Polyols upon Stabilization of Poly-Vinyl Chloride, *Journal of Applied Polymer Science*, vol. 25, pp. 887-900, (1980).
Mack, "Stabilizers", *Modern Plastics Encyclopedia*, (reprint copyright 1964 by McGraw and Hill, Inc.).
Technical Bulletin of Interstab Chemicals, Inc., entitled, "Calcium Zinc Stabilizers for Food Packaging", (date unknown).

*Primary Examiner*—Richard J. Apley
*Assistant Examiner*—Gregory Beaucage
*Attorney, Agent, or Firm*—Paul C. Flattery; Daniel D. Ryan

[57] ABSTRACT

A method of storing blood components uses a blood component storage container which is made of a plasticized polyvinyl chloride formulation which includes a heat stabilizer system selected from the group consisting of salts of $C_{10}$ to $C_{26}$ saturated fatty acids present in an amount of less than about one percent by weight of the composition. Surprisingly, use of only minimal amounts of these higher molecular weight fatty acids results in an effectively heat stabilized product suited for mass production techniques. As a result, the total amount of the heat stabilizer which can possibly leach into blood plasma is significantly reduced. The material from which the container is made preferably includes an effective amount of a plasticizer which is also essentially nonextractable in blood plasma.

8 Claims, 1 Drawing Figure

BLOOD COMPONENT STORAGE CONTAINER AND METHOD UTILIZING A POLYVINYL CHLORIDE PLASTIC FORMULATION FREE OR ESSENTIALLY FREE OF LEACHABLE MATERIALS

FIELD OF THE INVENTION

The invention generally relates to polyvinyl chloride plastic formulations. More particularly, the invention relates to medical grade polyvinyl chloride plastic formulations suited for contact with human blood and its components.

BACKGROUND AND OBJECTS OF THE INVENTION

At the present time, over 12 million units of whole blood are collected from volunteer donors in the United States each year. With the advent of blood component therapy, approximately 60% to 80% of the whole blood collected today is not itself stored and used for transfusion. Instead, the whole blood is first separated into its clinically proven components, which are themselves individually stored and used to treat a multiplicity of specific conditions and diseased states.

The clinically proven components of whole blood include red cells, which can be used to treat chronic anemia; platelets, which can be used to treat thrombocytopenia; cryoprecipate, which is rich in Clotting Factor VIII (also known as AHF) and can be used to restore several of the clotting factors to patients; as well as numerous other plasma-based fractions, such as albumin, plasma protein fraction, gamma globulin, and various other specific coagulation protein concentrates.

The present consensus is that care of patients is improved by providing only the therapeutic components of whole blood which are required to treat the specific disease. The demand for therapeutic components of whole blood is thus ever-increasing. Likewise, the demand for safe and effective systems and methods for collecting, separating, and storing the therapeutic components of whole blood grows accordingly.

Typically, whole blood and its components are collected and stored in containers made of medical grade polyvinyl chloride plastic formulations. These formulations must, by necessity, include a plasticizer, because polyvinyl chloride is not itself flexible enough for use in these containers. A commonly used plasticizer for this purpose is di-2-ethylhexylphthalate (DEHP).

DEHP is known to leach, or extract, into human blood components which are stored in DEHP-plasticized polyvinyl chloride containers. While there are no known adverse physiological results which are linked to the leaching of DEHP into blood components, it is, of course, desirable to minimize, as much as possible, the contact between blood components and any material not normally found in the human body. This has, in part, led to the development of medical grade polyvinyl chloride formulations utilizing plasticizers which leach into blood components at significantly lesser rates than DEHP. An example of such an alternate plasticizer in commercial use in medical grade polyvinyl chloride plastic formulations is tri(2-ethylhexyl)trimellitate (hereinafter referred to as TEHTM). See, also, Warner et al., U.S. Pat. No. 4,280,497.

Polyvinyl chloride formulations also must, by necessity, include a heat stabilizer to prevent the polyvinyl chloride from undergoing heat degradation and color change during and after processing. The most commonly used heat stabilizer systems for medical grade plastics employ, as the principal operative component, epoxidized vegetable oils, such as epoxidized soybean and linseed oils.

The search for optimal blood component storage containers has overlooked the fact that, in the amounts present in conventional heat stabilizer systems, epoxidized vegetable oils also leach into human blood components. For example, the TEHTM-plasticized container disclosed in the above-cited Warner et al. patent employs, in combination with the essentially nonextractable plasticizer, an extractable heat stabilization system of epoxidized vegetable oils.

While there are no known adverse physiological effects which arise as a result of exposure of blood components to epoxidized vegetable oils, it is nevertheless desirable to find alternate, essentially nonleachable heat stabilization systems for medical grade polyvinyl chloride plastic formulations.

SUMMARY OF THE INVENTION

To achieve this and other objects, the invention provides a blood component storage container which is made of a plasticized polyvinyl chloride material which includes an essentially nonextractable heat stabilization system. Thus a polyvinyl chloride composition is provided which is suitable for making blood component storage containers that are free of significantly leachable components.

More particularly, the invention provides a polyvinyl chloride formulation which includes, in addition to an effective amount of a plasticizer, a heat stabilization system selected from the group consisting of at least one salt of $C_{10}$ to $C_{26}$ saturated fatty acids present in an amount of less than about one percent by weight of the composition.

Surprisingly, use of only minimal amounts of salts of these higher molecular weight fatty acids results in an effective heat stabilization system which is essentially nonextractable in blood plasma.

Preferably, the heat stabilizer is a salt of stearic acid. More preferably, the heat stabilizer is a zinc or calcium salt of stearic acid and most preferably is a mixture of zinc stearate and calcium stearate.

Preferably, the plasticizer used in the formulation is one which is also essentially nonextractable by blood plasma, such as TEHTM. A medical grade polyvinyl chloride plastic formulation which is free or essentially free of leachable materials results.

The invention also provides a container made of the polyvinyl chloride formulation heretofore described. In one embodiment, in which the plasticizer employed is TEHTM, the container is particularly well-suited for the storage of platelets.

The invention further provides a method of storing blood components, such as platelets and red blood cells, in a manner which minimizes, to the greatest extent possible, the exposure of the components to blood extractable substances. The method includes the step of enclosing the components in a container which is made of the polyvinyl chloride formulation heretofore described.

In accordance with another aspect of the present invention, a plastic container of the foregoing composition is provided having a concentrate of viable platelets stored therein which is suitable for intravenous use.

In accordance with still another aspect of the present invention, a method of storing platelets in a container is provided which avoids the significant addition of leached components from the container to the stored platelets while maintaining the viability of the platelets at an acceptable level. The method includes storing the platelets in a plastic container that is a plasticized and heat stabilized polyvinyl chloride composition free of significantly leachable components and is composed of polyvinyl chloride resin, an effective amount of tri(2-ethylhexyl)trimellitate for plasticizing the resin and less than about one percent by weight of the composition of a heat stabilization system selected from the group consisting of at least one salt of $C_{10}$ to $C_{26}$ saturated fatty acids.

Other features and advantages of the invention will be pointed out in, or will be apparent from, the specification and claims, as will obvious modification of the embodiment shown in the drawing.

Figure 1:
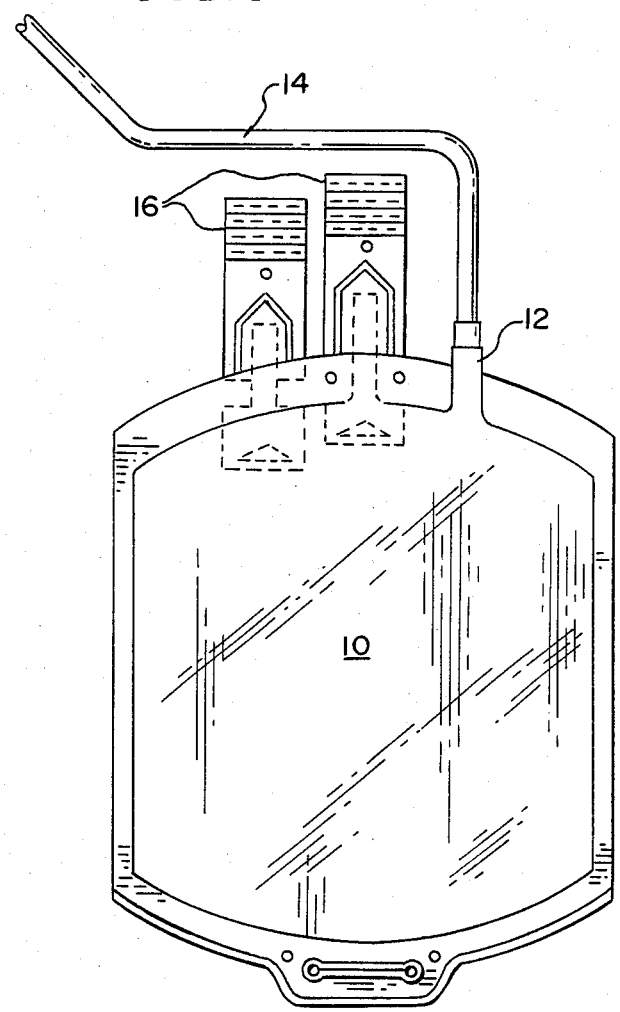
FIG. 1 is a plan view of a blood component container which is made of a polyvinyl chloride plastic formulation which embodies the features of the invention.

Before explaining the embodiments of the inventions in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

GENERAL DESCRIPTION OF THE INVENTION

A blood component storage container 10 is shown in FIG. 1. The container 10 may be variously configured. In the illustrated embodiment, the container 10 includes an inlet port 12 to which a length of flexible tubing 14 is integrally connected.

The tubing 14 may include, at its terminal end, a phlebotomy needle (not shown). In this arrangement, the tubing 14 serves to introduce whole blood from a donor into the container 10 for processing and, preferably, storage of certain of the components.

Alternately, the tubing 14 may communicate with the interior of another container (also not shown). In this arrangement, the tubing 14 serves to introduce a portion of the contents of the other container into the container 10 for additional processing and, preferably, storage.

Also, as illustrated, the container 10 includes a number of normally sealed, selectively openable access ports 16.

In accordance with the invention, the walls 18 of the container 10 are made of a plasticized medical grade polyvinyl chloride formulation which includes, in addition to an effective amount of a plasticizer, a heat stabilization system which is essentially nonextractable in blood plasma. Optionally, an effective antiblock agent is included.

THE PLASTICIZER

The plasticizer may be a fatty ester containing at least two ester linkages comprising fatty hydrocarbon groups of four to twelve carbon atoms. Examples of such ester materials include the dioctylphthalates and dioctyladipates, diisononylphthlate, and diisodecylphthalate.

The plasticizer may also be an ester of phosphoric acid containing at least two ester linkages comprising fatty hydrocarbon groups of 4 to 12 carbon atoms each. Examples of such ester materials include trioctylphosphate (specifically, tri(2-ethylhexyl)phosphate), trihexylphosphate, triheptylphosphate, and diisodecylphosphate.

The two classes of plasticizers just described are significantly extractable in blood plasma. At the end of the relevant storage period, these plasticizer are present in blood plasma the amount of at least 10 parts per million.

In keeping with the overall focus of the invention, the plasticizer utilized is preferably one which is essentially non-extractable by blood plasma. As used herein, a plasticizer which is "essentially non-extractable" by blood plasma is present in blood plasma in a concentration of no more than 2 parts per million at the end of the relevant storage period. Conventionally, the relevant storage period can be up to 35 days for whole blood (depending on the storage conditions and container) and up to about 5 days for platelets (depending on the storage conditions and container).

Such "essentially non-extractable" plasticizers include fatty esters containing at least three ester linkages comprising fatty hydrocarbon groups of 4 to 12 carbon atoms on each hydrocarbon chain.

Specific examples of such materials include tri-n-hexyl-trimellitate, trioctyltrimellitate, triisonoyl trimellitate, and tri(2-ethylhexyl)trimellitate (TEHTM).

The amount of plasticizer present in the formulation can vary according to the degree of flexibility desired. Compositions containing a relatively low quantity of plasticizer may be stiffer and less flexible than desired, while those with a relatively high quantity of plasticizer may be more pliable and flexible than desired.

As the amount of plasticizer is increased, mixing becomes more difficult and the likelihood of plasticizer leaching increases. On the other hand, as the amount of plasticizer decreases, gas permeability generally decreases, which may not be optimal for the storage of certain blood components, such as platelets.

Generally, an effective amount of plasticizer will be from about 25 to 90 parts per 100 parts resin by weight. Preferably, when the plasticizer is TEHTM, the amount of plasticizer is from about 63 to 85 parts per 100 parts resin by weight. Most preferably, the amount of TEHTM plasticizer is about 74 parts.

As the following Example 1 demonstrates, the amount of TEHTM present in the polyvinyl chloride formulation which embodies the features of the invention is essentially nonextractable in blood plasma.

EXAMPLE 1

An experiment was conducted to determine the accumulation of TEHTM in blood stored in containers of the following composition:

| Component | Parts by Weight |
| --- | --- |
| PVC Resin | 100 |
| Tri(2-ethylhexyl) trimellitate | 74 |
| Zinc Stearate/Calcium Stearate | 0.3 |
| Wax | 0.4 |

About 450 ml of whole blood was drawn into each of five containers of the above identified composition.

Each container also included an effective amount of CPD anticoagulant. The containers were stored at 4° to 2° C. for 35 days.

Samples were then extracted using the following procedure: One milliliter of whole blood was pipetted into a large test tube. Twenty milliliters of 2:1 chloroform:methanol solution (made of pesticide-grade solvents) was added to the test tube, and the contents of the tube were mixed on a vortex mixer at least three times within a 45-minute interval. The mixture was filtered through No. 41 filter paper into a 50-ml centrifuge tube containing 4 ml of an aqueous 0.24% sodium chloride solution. The contents of the centrifuge tubes were mixed on the vortex mixer, and the gases allowed to escape. The tubes were then stoppered and centrifuged at about 2900 rpm for ½ hour. After centrifugation, the water-methanol layer was aspirated off and discarded. The remaining chloroform layer was evaporated to dryness at about 60° C. under nitrogen. One milliliter of 2,2,4-trimethylpentane was added to each of the tubes repeatedly rinse the sides of the tubes with the solvent. The resulting solutions were quantitatively transferred to 1-ml volumetric flasks and diluted to volume. These blood samples were stored under refrigeration until analyzed.

The extracted samples were analyzed by gas chromotography under the following conditions:

| Column: | 3% OV-1 on Supelcoport 100/120 mesh 6 ft × ⅛ in. OD nickel |
|---|---|
| Detector: | Electron capture detector (ECD) at 350° C. |
| Injector temperature: | 330° C. |
| Column oven temperature: | 285° C. isothermal |
| Flow rate: | carrier $N_2$, 48 ml/minute makeup $N_2$, 30 ml/minute |
| Retention time: | approximately 4.2 minutes |
| Run time: | 10 minutes |

All samples analyzed showed TEHTM present in amounts less than 0.1 parts per million.

THE HEAT STABILIZATION SYSTEM

Plasticized polyvinyl chloride formulations require the presence of heat stabilizers before they can be processed into finished products. Without heat stabilizers, the polyvinyl chloride formulations would catastrophically degrade during processing as a result of the known so-called "HCl zipper effect".

Conventional heat stabilization system for FDA-approved medical grade polyvinyl chloride formulation include, as the principal operative component, epoxidized vegetable oils present in an amount greater than 3% by weight. Some conventional systems also include, in combination with the epoxidized oils, amounts of metal soaps, such as zinc or calcium stearate. These metal soaps have been observed to create a synergistic effect when used in combination with the epoxidized oils.

While the use of epoxidized oils results in a heat stabilized product suited for mass production techniques, as the following Example 2 demonstrates, epoxidized oils leach in measurable amounts in blood plasma.

EXAMPLE 2

An experiment was conducted to determine the accumulation of epoxidized oil plasticizer in blood stored in PVC blood bags heat stabilized with epoxidized vegetable oil under specific conditions.

The PVC material contained 9.2 parts of an epoxidized soybean oil per 100 parts PVC resin and 4.8 parts of tetrahydrofurfuryl oleate per 100 parts resin. Blood units were obtained from healthy volunteers and placed into individual bags containing a usual amount of CPD anticoagulant and stored at either 4° C. or 25° C. After storage, the blood samples were analyzed for epoxidized oil by analytical thin layer chromatography. The following results were obtained:

| Storage Temperature (°C.) | Storage Time (Weeks) | Epoxidized Oil Detected in Plasma Mean ppm + standard deviation) |
|---|---|---|
| 4 | 1 | 3.2 + 1.7 |
| 4 | 2 | 5.0 + 0.9 |
| 4 | 3 | 7.1 + 1.1 |
| 4 | 6 | 11.2 + 5.0 |
| 25 | 1 | 8.2 + 6.0 |
| 25 | 2 | 10.5 + 4.6 |
| 25 | 3 | 20.9 + 8.3 |
| 25 | 6 | 65.5 + 56.8 |

Epoxidized oils can be removed entirely from the heat stabilization system of a plasticized medical grade polyvinyl chloride formulation and still create a heat stabilized product suited for storing blood and blood components, which formulation is suited for mass production. In accordance with the invention, medical grade PVC compositions can be heat stabilized such that the exposure of blood extractable components is minimized.

In accordance with the invention, the formulation of the polyvinyl chloride material includes a heat stabilization system selected solely from the group consisting of salts of $C_{10}$ to $C_{26}$ saturated fatty acids. The system generally should be present in an amount of less than about one percent by weight of the composition.

The heat stabilization system is essentially non-extractable in blood plasma. It is believed this is because these salts, unlike epoxidized oils, are solids at room temperature. Furthermore, these salts of the higher molecular weight fatty acids tend to be quite stable. In addition, these salts are effective heat stabilizers by themselves in only minimal amounts.

EXAMPLE 3

An experiment was conducted to determine the accumulation of calcium and zinc in anticoagulant stored in containers in accordance with the invention. The anticoagulant utilized was the CPD type, which is commonly used with blood storage in a ratio of about 400 ml blood:40 ml CPD. The CPD was stored for significantly longer periods of time than would be encountered in blood storage, where the maximum period would be about 50 days. The following results were obtained for storage of samples at two temperatures:

| Storage Temperature | Storage Interval | Concentration (ppm) of Calcium and Zinc in the CPD at the storage interval | | |
|---|---|---|---|---|
| | | 6 mos. | 12 mos. | 24 mos. |
| Room Temperature | Ca | 1.13 | 1.01 | 1.04 |
| | Zn | 1.15 | 1.15 | 1.23 |
| 45° C. | Ca | 1.32 | | |
| | Zn | 1.41 | | |

Each storage interval tested was on a different container. Initially no Ca or Zn was present in the CPD. The data indicates that the amount of zinc and calcium leached into the CPD, and thus, of the heat stabilization system, is extremely low. Since the storage periods were extremely long relative to the anticipated storage periods of blood and blood components, it would be expected that the amount of leaching after a normal storage period would be substantially less.

THE ANTIBLOCK AGENT

Preferably, the formulation which embodies the features of the invention also includes an antiblock agent. Generally, when utilized, the antiblock agent will be present in an amount sufficient to provide the desired antiblock effect, or stated otherwise, to prevent adhesion of films made from the composition. The amount of antiblock agent will usually be from about 0.2 to about 0.6 parts per 100 parts resin by weight and preferably about 0.4 parts. As with the heat stabilization system, as the amount of antiblock increases, increased leaching can be anticipated. Thus, the preferred amount of antiblock agent is generally the minimum amount which will prevent adhesion of films made from the composition.

DESCRIPTION OF A PREFERRED EMBODIMENT

An especially preferred formulation which embodies the features of the invention includes, per 100 parts of polyvinyl chloride resin, 74 parts of tri(2-ethylhexyl)-trimellitate; 0.3 parts of a calcium stearate and zinc stearate heat stabilizer; and about 0.4 parts of a wax antiblock agent.

The polyvinyl chloride resin can be any suitable type. Those types of PVC resins which relatively easily absorb the plasticizer are preferred. Especially suitable resins are those known as "blotter" resins. One such preferred resin is marketed by B. F. Goodrich Chemical Co. under the trade designation "GEON 80X80". Another preferred resin is marketed by the Wacker Co. under the trade designation "VINNOL H70DF".

The plasticizer utilized in accordance with the invention, tri(2-ethylhexyl)trimellitate, is commercially available. One source is the Hatco Chemical Corp. marketing the plasticizer under the trade designation "Hatcol 200".

A 1:1 weight ratio of zinc stearate/calcium stearate is preferred. A suitable commercial source of the zinc stearate/calcium stearate combination is the Interstab Company which markets such a heat stabilizer under the trade designation "CZ-11-P". "CZ-11-P" is believed to be a 1:1 weight ratio of calcium stearate/zinc stearate. The "CZ-11-P" formulation may also contain minor amounts of calcium palmitate, zinc palmitate, and $C_{18}$ fatty acids.

The ingredients of the PVC composition of the invention can be suitably mixed by a blender. The PVC composition can be formed into sheets by conventional methods such as by calendaring or by extrusion to a desired thickness. A mixing screw type apparatus may be used in extruding the material. Generally, the materials are processed under suitable conditions so that unacceptable heat degradation or color change of the material does not occur. The type and amount of heat stabilizer will affect the processing conditions to which the composition may be subjected without the occurrence of significant degradation or color change. For example, a composition without calcium stearate is more likely to undesirably darken during processing than a composition containing calcium stearate and zinc stearate.

The antiblock agent which may be present generally may be any material that provides the desired antiblock effect without an undesired degree of leaching and which is not otherwise objectionable. Preferred antiblock agents are low viscosity, high melting point waxes, such as wax marketed under the trade designation "Acrawax C" by Glyco Chemicals, Inc. High viscosity oils may also be utilized. However, in general, oils will leach to a greater degree than waxes. Mixtures of antiblock agents may also be used.

The ingredients of the formulation of the invention can be suitably mixed by a blender. The formulation can be formed into sheets by conventional methods such as by calendaring or by extrusion to a desired thickness. A mixing screw type apparatus may be used in extruding the material.

Generally, the materials are processed under suitable conditions so that unacceptable heat degradation or color change of the material does not occur. The type and amount of heat stabilizer will affect the processing conditions to which the composition may be subjected without the occurence of significant degradation or color change. For example, a composition without calcium stearate is more likely to undesirably darken during processing than a composition containing both calcium stearate and zinc stearate. This is a reason why a mixture of calcium and zinc stearates is preferred.

Containers or bags can be made from the sheets of the composition utilizing conventional techniques, such as heat sealing. The resulting containers or bags should be sterilizable.

As before stated, containers or bags made in accordance with the invention may be utilized to store whole blood and whole blood components, including platelets and platelet concentrate. In this context, the containers or bags may be utilized either as the donor bag or as the transfer bag in a disposable blood component collection system, for example, a multiple blood bag system such as the one disclosed in U.S. Pat. No. 4,222,379.

The wall thickness of the container or bag formed of sheets of the composition should preferably be such that suitable strength is provided to withstand centrifugation and heat sterilization. However, if the container or bag is to be used to store platelets, the wall thickness should not be so great so as to prevent adequate $CO_2$ transport through the container walls during platelet storage. Inadequate $CO_2$ transport has been observed to lead to an unacceptable pH decrease of the platelets during storage. Generally, the $CO_2$ transport should be sufficient so that the pH of the platelets does not drop below 6.0 during storage.

The wall thickness of the container or bag will usually be in the range of from about 0.01 to 0.02 inch and preferably from about 0.0135 to 0.015 inch.

The present invention can be further understood by reference to the following additional examples.

EXAMPLE 4

Blood bags made in accordance with the invention were evaluated for platelet storage over five days. Chemical, aggregometric and morphological indices of viability of the stored platelet cells were evaluated. The specific indices of viability measured during storage included chemical changes (pH, $P_{CO_2}$, $P_{O_2}$, lactic acid, bicarbonate buffer and glucose), aggregation response changes to stimuli (thrombin collagen and ADP) and morphological changes as assessed by light microscopy.

MATERIALS AND METHODS

Storage Bags—The platelet concentrate storage bags were of the following composition:

| Component | Parts by Weight |
|---|---|
| PVC Resin | 100 |
| Tri(2-ethylhexyl)trimellitate (Hatcol 200) | 74 |
| Zinc Stearate/Calcium Stearate (CZ-11-P) | 0.3 |
| Wax (Acrawac C) | 0.4 |

Whole Blood—Six units of whole human blood were collected from ABO compatible volunteer donors into CPD anticoagulant contained by standard primary packs of Travenol Laboratories, Inc.

Platelet Rich Plasma—Platelet Rich Plasma (PRP) was made from whole blood (WB) using a Sorvall RC-3 centrifuge (HG-4L rotor) at 1900 rpm (4000xg) for six (6) minutes on timer (time to include initial acceleration of the centrifuge). PRP was expressed and pooled from the individual packs into a 2000 ml transfer pack. The PRP was weighed and equal amounts were utilized for each of the study packs (235 g/pack).

Platelet Concentrate—Platelet Concentrate (PC) was prepared in each of the study packs by centrifugation of the PRP at 4000 rpm (4100 xg) for six (6) minutes (time includes acceleration of the centrifuge). All but approximately 50 ml of plasma was expressed from the platelet pellet and the pellet was maintained undisturbed at room temperature for approximately one (1) hour and then vigorously resuspended in the 50 ml plasma volume.

Agitation—An Eberback shaker modified with a wire platform to allow good air access to both sides of the platelet storage packs was used. A horizontal shaking action was used at approximately 70 cycles per minute with a one (1) inch stroke. Packs were stored at ambient temperature (between 20°-24° C.).

Samples—Samples were withdrawn aseptically through a previously inserted medication injection site on the storage pack, after the site was vigorously scrubbed with a sterile alcohol swab. All remaining concentrates were cultured after the study to determine whether the platelets were contaminated during the storage period. No growth was detected in the samples cultured in both blood agar and thioglycollate media at 37° C. for at least 48 hours.

Morphology—Samples of PC were taken at various times during storage and put into two volumes of 0.5% glutaraldehyde in Ringer's buffer solution at room temperature. After one hour the fixed cells were sedimented, removed from the solution, and an additional two volumes of 3% glutaraldehyde in Ringer's buffer added. This preparation was stored at 4° C. overnight and then the liquid replaced with Ringer's solution. The cells were then analyzed by election microscopy. Ringer's solution was prepared to contain 115 mM NaCl, 15 mM $Na_2HPO_4$, 13 mM glucose, 5 mM KCl, 3 mM $NaH_2PO_4$, 2 mM $KH_2PO_4$, 1 mM $MgCl_2$ and 0.7 mM $MgSO_4$, pH=7.19. Cell morphology was estimated by light microscopy using the method of Kunicki et al., *Transfusion* 15:414, 1975.

pH, $P_{CO_2}$, and $P_{O_2}$—Measurements of pH, $P_{CO_2}$ and $P_{O_2}$ were made at 37° C. in the anaerobic chamber of a Radiometer BMS MK2 blood micro-system apparatus.

Bicarbonate Concentration—Bicarbonate concentration (buffer capacity) of the plasma was calculated according to the modified Henderson-Hasselbalch equation.

$$pH = pK_a + \log \frac{(HCO_3)}{0.03 \, (PCO_2)}$$

where $pK_a = 6.1$ at 37° C.
and pH and $PCO_2$ are also measured at 37° C.
$(HCO_3) = 0.03 \, PCO_2 \, (10^{(pH-6.1)})$ Lactate Concentration—Lactate concentrations were measured spectrophotometrically at 340 nm using an assay based on the LDH reduction of NAD to NADH during the conversion of lactic acid to pyruvate.

Glucose Concentration—Glucose was measured spectrophotometrically at 340 nm using a hexokinase enzyme assay method ("Statzyme" Glucose reagent kit, from Worthington Diagnostics).

Cell Counts—Cell concentrations were estimated by light microscopy.

Aggregometry—A "Bio Data Platelet Aggregation Profiler (PAP-3)" aggregometer was used. ADP ($3.33 \times 10^{-5}$, $1.82 \times 10^{-5}$ and $1.82 \times 10^{-6}$ M-Bio Data reagent) collagen (0.17 mg/ml-Bio Data reagent) and reconstituted, lyophilized thrombin (0.45, 0.18, and 0.09 units/ml, from Sigma Chemical) were used as the aggregation stimuli. For thrombin assays, cells were separated from plasma and resuspended in buffered Ringer's solution in a concentration range (similar to PRP) which allowed zero blanking of the PAP-3 instrument. For the ADP and collagen assays platelet concentrate (PC) was simply diluted with Ringer's buffer. Approximately one volume of sedimented PC cells to two to five volumes of Ringer's solution was used.

RESULTS

Pack Specifics—The characteristics of the individual packs including material of construction, pack size, plasma volume, cell concentration, and total number of cells per pack are set forth by Table 1.

Chemistries—Table 2 lists the results of PC chemistries at various periods during the 5-day storage study. These indicies include pH, $P_{CO_2}$, $P_{O_2}$, lactic acid, bicarbonate buffer, and glucose concentrations.

Morphology—Results of morphology scores assigned after light microscopy examination of stored cells are set forth in Table 2.

TABLE 1

| Bag # | Bag Size (ml) | Cell Count (cells/μl × $10^6$) | Total Volume (ml) | Total Cells (× $10^{11}$) |
|---|---|---|---|---|
| 1 | 300 | 1.73 | 49.6 | 0.858 |
| 2 | 600 | 1.85 | 54.2 | 1.003 |
| 3 | 600 | 1.26 | 53.0 | 0.668 |
| 4 | 600 | 1.39 | 58.2 | 0.809 |

TABLE 2

| | | | STORAGE DATA | | | | |
|---|---|---|---|---|---|---|---|
| Bag # | Storage Time (Hrs) | pH | Pco₂ (mmHg) | Po₂ (mmHg) | Lactic Acid (mg/dl) | Bicarbonate Buffer (mM) | Glucose | Morphology Score |
| 1 | 0.0 | 6.996 | 73.2 | 84.2 | 31.8 | 17.34 | 401 | 400 |
| 1 | 20.0 | 7.048 | 59.8 | 73.4 | 41.6 | 15.97 | 379 | 400 |
| 1 | 43.5 | 6.949 | 52.1 | 40.0 | 69.1 | 11.08 | 356 | 340 |
| 1 | 67.5 | 6.578 | 89.9 | 101.1 | 109.1 | 8.13 | 274 | 195 |
| 1 | 91.0 | 6.704 | 43.9 | 63.8 | 197.2 | 5.31 | 245 | 195 |
| 1 | 114.0 | 6.690 | 35.9 | 71.2 | — | 4.20 | — | 175 |
| 2 | 0.0 | 7.015 | 66.7 | 67.4 | 32.9 | 16.51 | 400 | 400 |
| 2 | 20.0 | 7.134 | 44.9 | 72.1 | 39.6 | 14.62 | 368 | 380 |
| 2 | 43.5 | 7.112 | 39.8 | 49.0 | 71.2 | 12.32 | 342 | 360 |
| 2 | 67.5 | 7.048 | 40.4 | 95.0 | 88.8 | 10.79 | 309 | 300 |
| 2 | 91.0 | 7.026 | 32.2 | 70.2 | 138.8 | 8.17 | 279 | 300 |
| 2 | 114.0 | 6.939 | 26.9 | 81.4 | — | 5.59 | — | 280 |
| 3 | 0.0 | 7.032 | 68.5 | 62.5 | 31.1 | 17.63 | 392 | 400 |
| 3 | 20.0 | 7.143 | 44.5 | 67.4 | 38.0 | 14.79 | 374 | 400 |
| 3 | 43.5 | 7.092 | 38.2 | 84.0 | 71.8 | 11.29 | 338 | 360 |
| 3 | 67.5 | 7.062 | 39.2 | 87.1 | 86.6 | 10.81 | 310 | 300 |
| 3 | 91.0 | 6.984 | 30.3 | 78.4 | 144.8 | 6.98 | 274 | 270 |
| 3 | 114.0 | 6.921 | 27.4 | 68.0 | — | 5.46 | — | 270 |
| 4 | 0.0 | 7.043 | 66.6 | 62.3 | 31.2 | 17.58 | 393 | 400 |
| 4 | 20.0 | 7.138 | 44.5 | 68.2 | 37.8 | 14.62 | 372 | 390 |
| 4 | 43.5 | 7.135 | 40.1 | 70.0 | 66.0 | 13.08 | 351 | 340 |
| 4 | 67.5 | 7.066 | 42.7 | 75.0 | 83.4 | 11.88 | 313 | 280 |
| 4 | 91.0 | 7.035 | 32.6 | 68.1 | 129.4 | 8.45 | 284 | 270 |
| 4 | 114.0 | 6.990 | 27.6 | 92.0 | — | 6.45 | — | 270 |

The pH of PC stored in 300 ml bags in accordance with the invention fell from an initial pH of approximately 7.1 to only 6.6 over a 5-day storage period. The pH stability was further enhanced in larger 600 ml bags and only ranged between 7.1 and 6.9 over the entire 5-day storage period. Similarly, good blowoff of $CO_2$ was noted in PC contained by the 600 ml bags (maximum $Pco_2$ 116 mm Hg) during the initial (high metabolic flux) storage period of the PC.

The results of Example 4 demonstrate the suitability of bags in accordance with the invention for storing platelet concentrates.

EXAMPLE 5

Containers of the same composition as foregoing Example 4 were also evaluated for storage of whole blood.

Ten of the containers were used in the study. These will be hereafter identified as V-1035 containers. Five DEHP-plasticized polyvinyl chloride containers (heat stabilized principally with epoxidized vegetable oils) were also utilized as controls and for comparison purposes. These will hereafter be referred to as PL-130 containers.

Blood (about 450 ml) was collected into each of the containers from normal donors over a two-day period. Blood was mixed frequently by inversion of bags during collection. The collection times were similar for all units.

Whole blood was kept in the containers for the duration of the study. The blood was stored at 4° to 6° C. and sampled at 1, 7, 14 and 21 days after collection. At each time period, sampling was done by manually inverting a unit to mix the sedimented red cells with the plasma, then aseptically removing a total of about 14 ml of blood through an injection site with three sterile syringes. Blood drawn into the first syringe was discarded to eliminate the chance of assaying unmixed blood trapped in the injection site. Blood samples in two other syringes were analyzed for pH, $PO_2$, $PCO_2$, and microaggregate particle volume within one hour of sampling. In addition, material was removed for plasma hemoglobin, ATP, and 2, 3, DPG analyses by analytical methods described in previous studies.

All units were checked for sterility at the end of the study by the use of sheep blood agar plates and thioglycollate broth tubes. This confirmed that sterility was maintained in all the units throughout the study.

The results are summarized in Table 1.

TABLE 1

Comparison of Blood Stored in Containers Fabricated in Accordance with The invention with Blood Stored in Conventional BLOOD-PACK ® Units

| Days of Storage 4° = 2° C. | Plasma Hemoglobin (mg %) | | pH | | $PO_2$ (mm Hg) | | $PCO_2$ (mm Hg) | | ATP (μM/g Hgb) | | 2,3 DPG (μm/g Hb) | | MPV (μ³ × 10³/mm³) | |
|---|---|---|---|---|---|---|---|---|---|---|---|---|---|---|
| | V-1035 | PL-130 | V-1035 | PL-130 | V-1035 | PL-130 | V-1035 | PL-1035 | V-1035 | PL-1035 | V-1035 | PL-130 | V-1035 | PL-130 |
| 1 | 9.5 ± 2.3 | 9.0 ± 2.7 | 6.932 ± 0.049 | 6.986 ± 0.029 | 35.5 ± 5.7 | 33.1 ± 3.0 | 84.4 ± 14.7 | 90.1 ± 7.1 | 2.6 ± 0.4 | 2.2 ± 0.2 | 1.5 ± 1.4 | 2.0 ± 0.6 | 343 ± 770 | 330 ± 9 |
| 7 | 17.3 ± 5.3 | 14.3 ± 2.9 | 6.922 ± 0.183 | Not Observed | 42.2 ± 7.3 | 35.1 ± 9.4 | 109.2 ± 9.3 | 96.3 ± 4.9 | 2.6 ± 0.4 | 2.5 ± 0.3 | 1.4 ± 1.3 | 1.1 ± 0.2 | 1448 ± 1372 | 2513 ± 241 |
| 14 | 20.9 ± 7.8 | 16.4 ± 4.4 | Not Observed | Not Observed | 74.0 ± 27.7 | 41.4 ± 4.0 | 113.0 ± 7.2 | 115.7 ± 7.9 | 2.5 ± 1.4 | 2.3 ± 0.5 | 0.9 ± 0.5 | 0.8 ± 1.6 | 1003 ± 342 | 145 ± 33 |
| 21 | 40.1 ± 13.2 | 17.4 ± 1.3 | 6.680 ± | 6.682 ± | 47.9 ± 5.8 | 38.0 ± 8.3 | 114.1 ± | 112.3 ± | 2.4 ± 0.4 | 2.8 ± 0.4 | 0.3 ± 0.2 | 0.4 ± 0.3 | 903 ± 291 | 154 ± 15 |

TABLE 1-continued

Comparison of Blood Stored in Containers Fabricated in Accordance with
The invention with Blood Stored in Conventional BLOOD-PACK ® Units

| Days of Storage 4° = 2° C. | Plasma Hemoglobin (mg %) V-1035 | Plasma Hemoglobin (mg %) PL-130 | pH V-1035 | pH PL-130 | $PO_2$ (mm Hg) V-1035 | $PO_2$ (mm Hg) PL-130 | $PCO_2$ (mm Hg) V-1035 | $PCO_2$ (mm Hg) PL-1035 | ATP ($\mu M/g$ Hgb) V-1035 | ATP ($\mu M/g$ Hgb) PL-1035 | 2.3 DPG ($\mu m/g$ Hb) V-1035 | 2.3 DPG ($\mu m/g$ Hb) PL-130 | MPV ($\mu^3 \times 10^3/mm^3$) V-1035 | MPV ($\mu^3 \times 10^3/mm^3$) PL-130 |
|---|---|---|---|---|---|---|---|---|---|---|---|---|---|---|
| Significance of Difference at 21 Days | $P < 0.05$ | | 0.021 None | 0.031 | $P < 0.05$ | | 14.5 None | 9.3 | None | | None | | None | |

RESULTS

As can be seen in Table 1, only the plasma hemoglobin content of blood stored in V-1035 packs differed from that of blood stored in PL-130 packs. While there was also a difference in $PO_2$ concentration at 21 days, this difference was probably artifactual, because no concomitant difference in $PCO_2$ levels was observed.

As the foregoing Example 4 demonstrates, a container which is made of a polyvinyl chloride plastic formulation which embodies the features of the invention is well-suited for use to store whole blood (or red blood cells).

Various of the features of the invention are set forth in the following claims.

We claim:

1. A method of storing platelets in a manner which minimizes the exposure of the platelets to blood extractable substances, said method comprising the step of storing the platelets in a flexible, plastic container, comprising a plasticized and heat stabilized polyvinyl chloride composition free of significantly leachable components and composed of polyvinyl chloride resin, an effective amount of tri(2-ethylhexyl) trimellitate for plasticizing said resin and a heat stabilization system selected from the group consisting of salts of $C_{10}$ to $C_{26}$ saturated fatty acids present in said polyvinyl chloride composition in an amount of from about 0.26 to about 0.35 parts per 100 parts resin by weight.

2. The method of claim 1 wherein said polyvinyl chloride composition further comprises an effective amount of an antiblock agent.

3. The method of claim 1 wherein said polyvinyl chloride composition comprises from about 25 to about 90 parts tri(2-ethylhexyl)trimellitate per 100 parts resin by weight.

4. The method as recited in claim 1 wherein said polyvinyl chloride composition comprises about 74 parts of tri(2-ethylhexyl)trimellitate per 100 parts resin by weight.

5. The method of claim 1 wherein said heat stabilization system contains calcium and zinc stearate in a weight ratio of about 1 part calcium stearate to 1 part zinc stearate.

6. The method of claim 5 wherein said polyvinyl chloride composition comprises, by weight, about 100 parts of resin, about 74 parts of tri(2-ethylhexyl)trimellitate, 0.3 parts of said heat stabilization system containing calcium stearate and zinc stearate in a weight ratio of about 1 part calcium stearate to 1 part zinc stearate and 0.4 parts of a wax antiblock agent.

7. The method of claim 1 wherein the walls of the container have a thickness of from about 0.01 to about 0.20 inch.

8. A method of storing blood components in a manner which minimizes the exposure of the components to blood extractable substances, said method comprising the step of enclosing the components in a container made of a plasticized polyvinyl chloride material which includes a polyvinyl chloride resin, a effective amount of a plasticizer which is essentially nonextractable in blood plasma, and a heat stabilization system comprising at least one compound selected from the group consisting of salts of $C_{10}$ to $C_{26}$ saturated fatty acids present in an amount of from about 0.26 to about 0.35 parts per 100 parts resin by weight and no other heat stabilizer material.

* * * * *